(12) United States Patent
Neumann

(10) Patent No.: US 7,011,735 B1
(45) Date of Patent: Mar. 14, 2006

(54) ARRANGEMENT FOR WIRING AN ELECTROCHEMICAL SENSOR

(75) Inventor: Harald Neumann, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/369,767

(22) Filed: Aug. 6, 1999

(30) Foreign Application Priority Data

Aug. 7, 1998 (DE) ................................ 198 35 766

(51) Int. Cl.
*G01N 27/409* (2006.01)
*G01N 27/41* (2006.01)

(52) U.S. Cl. ...................................... 204/427; 204/424
(58) Field of Classification Search ................ 204/426, 204/408, 425, 424, 427
See application file for complete search history.

(56) References Cited

U.S. PATENT DOCUMENTS

| 4,365,604 A | * | 12/1982 | Soné ........................... 204/424 |
| 4,400,260 A | | 8/1983 | Stahl et al. |
| 4,629,549 A | * | 12/1986 | Kojima et al. .............. 204/406 |
| 4,787,966 A | * | 11/1988 | Nakajima et al. ........... 204/406 |
| 4,814,059 A | * | 3/1989 | Nishizawa et al. ......... 204/406 |
| 4,839,019 A | * | 6/1989 | Takahama et al. .......... 204/425 |
| 4,909,922 A | * | 3/1990 | Kato et al. .................. 204/406 |
| 5,203,983 A | * | 4/1993 | Ohyama et al. ............. 204/427 |
| 5,413,683 A | * | 5/1995 | Murase et al. .............. 204/426 |

OTHER PUBLICATIONS

Logothetis et al, "High-temperature oxygen sensors based on electrochemical oxygen pumping", from Fundamentals and Applications of Chemical Sensors, ACS Symposium Series 309, pp. 136-154, 1986.*

Liu et al "Oxygen Sensors", Engineered Materials Handbook, vol. 4, Ceramics and Glasses, pp. 1131-1139, 1991.*

* cited by examiner

*Primary Examiner*—Kaj K. Olsen
(74) *Attorney, Agent, or Firm*—Kenyon & Kenyon

(57) ABSTRACT

An electrochemical sensor, in particular for determining the oxygen content in exhaust gases of internal combustion engines, has a solid electrolyte element having at least one first electrode, at least one second electrode, and at least one heating element. The second electrode located to the heating element is connected to ground, and the first electrode coacting with the second electrode is negatively polarized, a negative operating voltage being provided.

20 Claims, 2 Drawing Sheets

ARRANGEMENT FOR WIRING AN ELECTROCHEMICAL SENSOR

BACKGROUND INFORMATION

Electrochemical solid electrolyte sensors, in particular for determining the oxygen content in exhaust gases of internal combustion engines, operate according to the so-called Nemst principle, according to which an electromotive force (EMF) is picked off, as the probe voltage, between a reference electrode having an excess of oxygen and a measurement electrode to which the measured gas is applied. The EMF occurs if an oxygen concentration $\lambda<1$ is present in the measured gas, stoichiometric conditions being present in the measured gas when $\lambda=1$. The probe voltage is conveyed to a control device as a measurement signal. Electrochemical solid electrolyte sensors require a temperature of at least 300° C. in order to operate. An electrical resistance heater, operated with a heating voltage that corresponds (when the sensor is used in a motor vehicle) to the vehicle's battery voltage, is integrated into the solid electrolyte sensor for that purpose. The reference electrode of the solid electrolyte sensor is connected as the positive electrode. The measurement electrode is connected to ground (negative pole). When solid electrolyte sensors are operated, it if found that coupling of the heat voltage into the probe voltage occurs. This falsifies the measurement signal. It has already been proposed to separate the sensing element and the heater from one another, or to provide between the heater and the adjacent electrode a shielding electrode to dissipate the coupled-in voltage (see German Patent Application No. 31 20 159).

SUMMARY OF THE INVENTION

The arrangement according to the present invention has the advantage that coupling of the heater voltage can effectively be blocked with simple means.

Coupling is most effectively prevented if the electrode adjacent to the resistance heater lies in a layer plane of the solid electrolyte element, and has at least approximately the surface extent of the further electrode.

DETAILED DESCRIPTION

Figure 1:
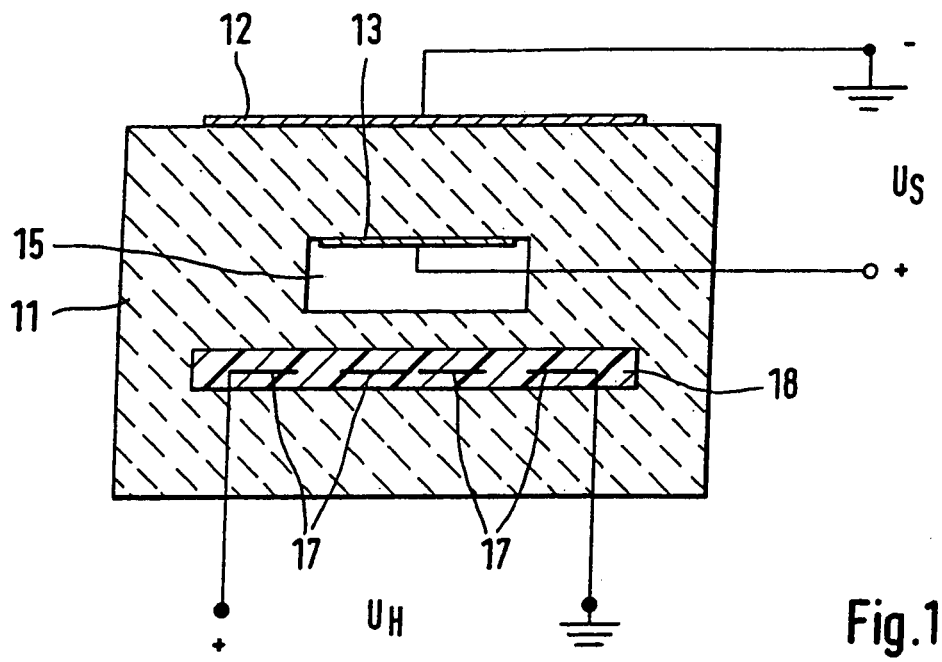
FIG. 1 shows a cross section through a solid electrolyte sensor having a wiring layout as defined in the existing art.

FIG. 1 shows an electrochemical oxygen sensor with a schematic depiction of an electrical wiring layout. The sensor has a ceramic element 11 made of a ceramic that conducts oxygen ions (for example stabilized $ZrO_2$), a measurement electrode 12, and a reference electrode 13. Measurement electrode 12 is exposed to a measured gas. Reference electrode 13 is arranged in a reference duct 15 that communicates with a reference gas, e.g. air. An electrical resistance heating element 17 that is embedded in an electrical insulator 18 is integrated into ceramic element 11.

The electrical wiring layout of electrodes 12, 13, and resistance heater 17 is depicted schematically, resistance heater 17 being operated with a heating voltage $U_H$ of, for example, 12 V. The negative terminal is connected to ground. Measurement electrode 12, constituting the negative electrode, is also connected to ground. Reference electrode 13 is operated as the positive electrode.

Figure 2:
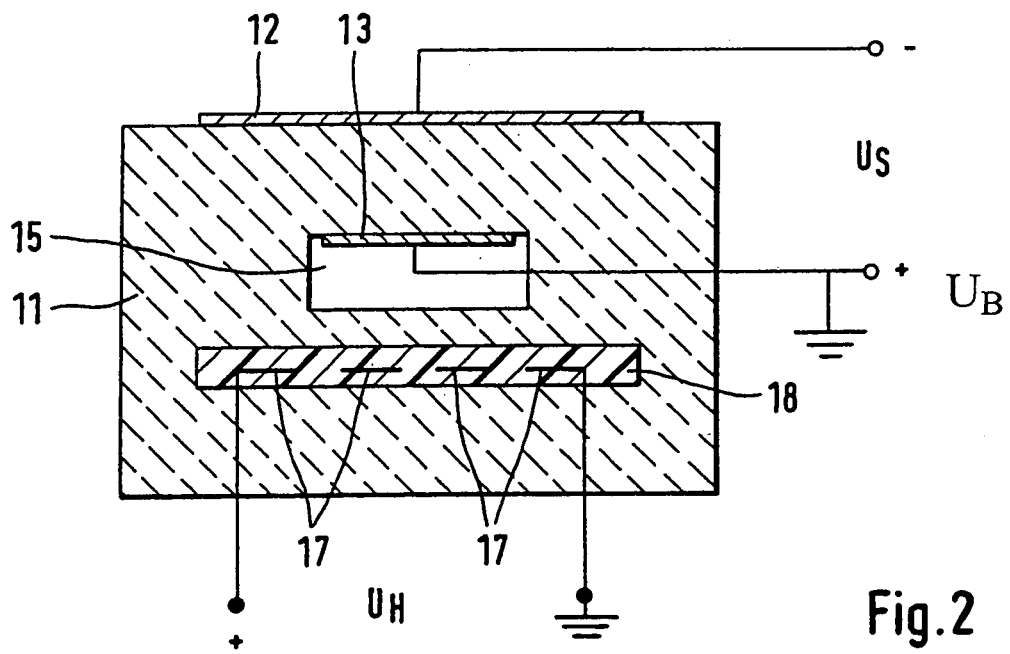
FIG. 2 shows a cross section through a first exemplary embodiment of a solid electrolyte sensor in accordance with the wiring layout according to the present invention.

FIG. 2 shows the same solid electrolyte sensor as in FIG. 1, but with the electrical wiring layout according to the present invention, according to which reference electrode 13, constituting the positive electrode, is connected to ground. Measurement electrode 12 is wired as the negative electrode. According to the present invention, the electrode located closest to resistance heater 17—which in the present case is reference electrode 13—is connected to ground. A negative probe voltage $U_S$ is thereby created. The result is that a negative operating voltage $U_B$, which powers a circuit arrangement for analyzing the negative probe voltage $U_S$, is made available via a circuit that is known per se. The necessary circuit for generating a negative operating voltage $U_S$ is known per se and available to one skilled in the art.

Figure 3:
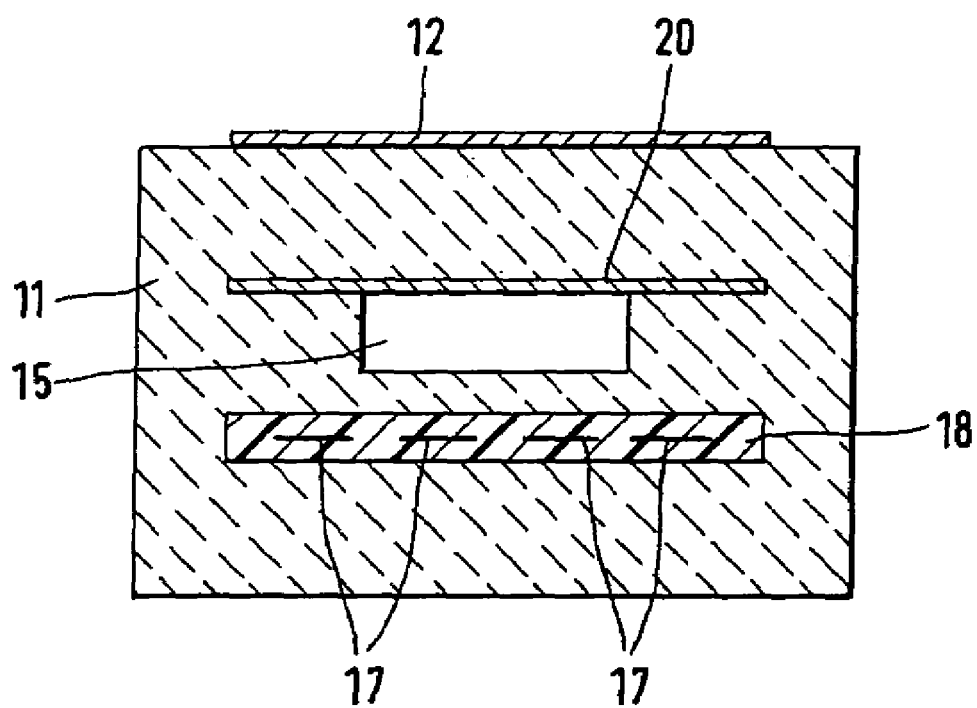
FIG. 3 shows a cross section through a second exemplary embodiment of an electrochemical solid electrolyte sensor.

A further exemplary embodiment of an oxygen sensor is evident from FIG. 3. What is arranged here is a reference electrode 20 that extends over the width of reference duct 15 and possesses, approximately in the layer plane, the surface extent of measurement electrode 12. The larger-area reference electrode 20 thus additionally acts as a shield against any coupling of heater voltage $U_H$ into measurement electrode 12. The further elements of the exemplary embodiment in FIG. 3 correspond to the exemplary embodiment in FIG. 2.

The present invention is not limited to the exemplary embodiments of planar oxygen sensors described above. It is just as conceivable also to utilize the proposed electrical wiring layout in solid electrolyte sensors of so-called finger shape, i.e. having a solid electrolyte element that is constituted by a solid electrolyte tube that is closed on one side.

The wiring layout according to the present invention is moreover also usable in electrochemical pump cells in which oxygen is pumped by application of a pump voltage, and the limiting current which flows in that context is utilized as the measurement signal. The negative operating voltage $U_B$ is used in this context as the pump voltage.

The invention claimed is:

1. An electrochemical sensor comprising:
   a solid electrolyte element including at least one first electrode, at least one second electrode and at least one heating element, the at least one second electrode being situated closer than the at least one first electrode to the at least one heating element, the at least one second electrode being coupled to ground, the at least one first electrode coating with the at least one second electrode and being negatively polarized;
   wherein the second electrode is in a reference duct and wherein the reference duct is situated between the at least one first electrode and the at least one heating element.

2. The sensor according to claim 1, further comprising an arrangement for providing a negative operating voltage so that coupling of a heater voltage is effectively blocked and wherein the negative operating voltage is applied to the negatively polarized electrode.

3. The sensor according to claim 2, further comprising a measurement circuit, the negative operating voltage powering the measurement circuit.

4. The sensor according to claim 2, further comprising a circuit arrangement for analyzing a negative probe voltage ($U_S$), and wherein the negative operating voltage ($U_B$) powers the circuit arrangement. voltage ($U_B$) powers the circuit arrangement.

5. The sensor according to claim 1, wherein the at least one second electrode lies in a layer plane of the solid electrolyte element, the at least one second electrode having approximately the same surface size as the at least one first electrode.

6. The sensor according to claim 1, wherein the at least one second electrode is a reference electrode communicating with a reference atmosphere, and the at least one first electrode is a measurement electrode.

7. The sensor according to claim 1, wherein the solid electrolyte element is a ceramic element.

8. The sensor according to claim 1, wherein the solid electrolyte element is $ZrO_2$.

9. The sensor according to claim 1, wherein a heating voltage of 12 V is applied to the at least one heating element.

10. The sensor according to claim 1, wherein the at least one heating element is embedded in an electrical insulator.

11. The sensor according to claim 1, wherein a portion of the second electrode extends over the width of a reference duct and additionally acts as a shield against any coupling of heater voltage $U_H$ and wherein the reference duct is situated between the at least one first electrode and the at least one heating element.

12. The sensor according to claim 1, wherein a heating voltage is applied to the at least one heating element.

13. The sensor according to claim 1, wherein the solid electrolyte element includes a solid electrolyte tube that is closed on one side.

14. The sensor according to claim 13, further comprising an arrangement to provide a negative operating voltage so that a coupling of a heater voltage is effectively blocked, the negative operating voltage being applied to the negatively polarized electrode.

15. The sensor according to claim 14, further comprising a measurement circuit, the negative operating voltage powering the measurement circuit.

16. The sensor according to claim 13, wherein the solid electrolyte element includes a ceramic element.

17. The sensor according to claim 13, wherein the solid electrolyte element includes $ZrO_2$.

18. An electrochemical sensor comprising:
a solid electrolyte element including at least one first electrode, at least one second electrode and at least one heating element, the at least one second electrode being situated closer than the at least one first electrode to the at least one heating element, the at least one second electrode being coupled to ground, the at least one first electrode coating with the at least one second electrode and being negatively polarized;

an arrangement to provide a negative operating voltage so that a coupling of a heater voltage is effectively blocked, the negative operating voltage being applied to the negatively polarized electrode; and a circuit arrangement for analyzing a negative probe voltage, the negative operating voltage powering the circuit arrangement;

wherein the solid electrolyte element includes a solid electrolyte tube that is closed on one side.

19. An electrochemical sensor arrangement comprising:

a solid electrolyte element including a reference duct, $ZrO_2$, at least one first electrode, at least one second electrode, at least one heating element and a reference duct situated between the at least one first electrode and the at least one heating element, the at least one second electrode coupled to ground, having approximately the same surface size as the at least one first electrode, lying in a layer plane of the solid electrolyte element, and situated inside the reference duct closer than the at least one first electrode to the at least one heating element, the at least one first electrode coacting with the at least one sound electrode and being negatively polarized;

an arrangement to provide a negative operating voltage so that a coupling of a heater voltage is effectively blocked, the negative operating voltage being applied to the negatively polarized electrode;

a measurement circuit, the negative operating voltage powering the measurement circuit; and a circuit arrangement to analyze a negative probe voltage, negative operating voltage powers the circuit arrangement.

20. The sensor according to claim 19, wherein the solid electrolyte element includes a solid electrolyte tube that is closed on one side.

* * * * *

UNITED STATES PATENT AND TRADEMARK OFFICE
CERTIFICATE OF CORRECTION

PATENT NO. : 7,011,735 B1
APPLICATION NO. : 09/369767
DATED : March 14, 2006
INVENTOR(S) : Harald Neumann Page 1 of 1

It is certified that error appears in the above-identified patent and that said Letters Patent is hereby corrected as shown below:

Column 1, line 26, change "if it found that" to-- it is found that--

Column 3, lines 2-3, delete "voltage ($U_B$) powers the circuit arrangement."

Signed and Sealed this

Second Day of January, 2007

JON W. DUDAS
*Director of the United States Patent and Trademark Office*